United States Patent [19]

Borden et al.

[11] Patent Number: 5,606,418
[45] Date of Patent: Feb. 25, 1997

[54] QUASI BRIGHT FIELD PARTICLE SENSOR

[75] Inventors: Peter G. Borden, San Mateo; Derek G. Aqui, San Jose, both of Calif.

[73] Assignee: High Yield Technology, Inc., Sunnyvale, Calif.

[21] Appl. No.: 414,145

[22] Filed: Mar. 29, 1995

Related U.S. Application Data

[63] Continuation of Ser. No. 41,070, Apr. 1, 1993, abandoned.
[51] Int. Cl.$^6$ ................................................. G01N 15/02
[52] U.S. Cl. ............................. 356/364; 356/338; 606/11
[58] Field of Search ........................... 356/335, 336, 356/337, 338, 364, 365, 368, 370; 606/10, 11, 1, 2, 3

[56] References Cited

U.S. PATENT DOCUMENTS

| | | | |
|---|---|---|---|
| 3,809,478 | 5/1974 | Talbot | 356/335 |
| 4,653,760 | 3/1987 | Dyer et al. | 273/310 |
| 4,799,796 | 1/1989 | Musha | 356/336 |
| 4,930,865 | 6/1990 | Dosman | 356/326 |
| 5,005,977 | 4/1991 | Tomoff | 356/367 |
| 5,133,602 | 7/1992 | Batchelder et al. | 356/364 |

FOREIGN PATENT DOCUMENTS

| | | | |
|---|---|---|---|
| 2254144 | 9/1992 | United Kingdom | 356/368 |

*Primary Examiner*—Angela D. Sykes
*Assistant Examiner*—Sonja Harris-Ogugua
*Attorney, Agent, or Firm*—Skjerven, Morrill, MacPherson, Franklin & Friel; Edward C. Kwok

[57] ABSTRACT

A structure and a method provide a quasi bright field particle sensor, using a laser beam of predetermined polarization. A phase shift caused by a particle passing through a laser beam is utilized to detect the presence of a particle. In one embodiment, the laser beam is split into two components of laser beams of orthogonal polarization separated by a predetermined distance, so as to allow detection of both spherical and non-spherical particles. In another embodiment, where only non-spherical particles are detected, a single laser beam is used.

18 Claims, 4 Drawing Sheets

Polarizarion without scatter

Polarizarion without scatter

QUASI BRIGHT FIELD PARTICLE SENSOR

This application is a continuation of application Ser. No. 08/041,070, filed Apr. 1, 1993, now abandoned.

BACKGROUND OF THE INVENTION

1. Field of the Invention

This invention relates to the use of polarized light to detect small particles. More specifically, this invention relates to a means for detection of a particle, using a change in angle of polarization in a linearly polarized light beam when the particle scatters light passing through a laser beam.

2. Discussion of the Related Art

Particle detection is widely used in vacuum process equipment, such as that involved in the processing of semiconductor wafers, because even a small number of particles in the manufacturing process can lead to substantial yield loss.

Most particle detectors or monitors are designed based on a dark field technique. Several examples of particle monitors using a dark field technique are disclosed in U.S. Pat. No. 4,739,177 to Peter Borden, entitled "Particle Detector for Wafer Processing Equipment," filed on Sep. 16, 1986 and issued on Jun. 19, 1988. In the dark field technique, a laser beam is projected through a region where particles are expected to pass, and photodetectors or photocells are placed off-axis near the laser beam to detect the light the particles scatter from the laser beam. In a dark field particle detector, the laser beam is not incident on the photodetector. (Hence, the term "dark field" technique.) The scattered light detected by the off-axis photodetector is converted to an electrical pulse that indicates the presence of the particle.

However, a dark field particle detector has numerous inherent limitations. In particular, such a particle detector is very sensitive to background light or noise. For example, when used as a particle detector in a sputtering process which uses plasma, light from plasma glows, or from dirt present on the optics, can scatter light from the laser beam to the photodetectors. Also, since the photodetectors of a dark field particle detector must be placed in close proximity to the laser beam, such a particle detector is inherently limited in where it can be deployed. In particular, such a dark field particle detector cannot be readily placed inside a processing chamber where the semiconductor wafers are being processed.

A bright field particle detector overcomes some of the difficulties encountered in the use of a dark field particle detector. In a "bright field" sensor or detector, a laser beam is shone directly on the sensing photodetector. Particles passing through the laser beam scatter light from the laser beam, thereby reducing its intensity and, consequently, reducing the photocell current when the laser beam impinges the photocell. Since a bright field particle detector does not require the photocells to be placed in close proximity to the laser beam along its path, the bright field technique allows the laser beam to be shone across processing chambers. Further, the bright field technique is inherently less sensitive to background light or noise, since the bright field detector receives only the input stimulus from a small angular aperture, which corresponds to the size of the laser beam. An example of bright field sensors 15 described in the copending application: Ser. No. 07/824,619, entitled "A Non-invasive Particle Monitor for sealed HDAs," by Peter Borden, assigned to High Yield Technology, filed on Jan. 23, 1992, attorney docket No. M-1794 U.S. Copending Application, "A Non-invasive Particle Monitor for Sealed HDAs" and "An in situ Real Time Particle Monitor for a Sputter Coater Chamber" is hereby incorporated by reference in their entirety.

Bright field sensors, however, are susceptible to shot noises. Thus, bright field sensors are traditionally regarded as lacking the requisite sensitivity for such applications as semiconductor wafer processing. Shot noise is the statistical noise generated in a photocell by the photon current, and is thus proportional to the square root of the laser power. The shot noise current in a photocell is given by the equation $$I_{shot} = \sqrt{2qPA(BW)} \tag{1}$$

where q is the charge of an electron, P is the power of the laser, A is the conversion efficiency of the photocell (in amperes per watt), and BW is the bandwidth of detection.

Because shot noise is typically much higher in power than amplifier noise, shot noise limits the sensitivity of the best bright field sensors to detection of particles. In the state of the art, bright field sensors have a sensitivity of about 1 µm.

SUMMARY OF THE INVENTION

The present invention discloses a "quasi bright field" sensor which, by reducing shot noise significantly, achieves both the advantages of a bright field sensor, and a higher sensitivity than a bright field sensor.

In accordance with one aspect of the present invention, a particle sensor has a laser source for providing a laser beam of a predetermined polarization. The laser beam is focussed to pass through an area of space in which particles to be detected are present. A polarizing optical component is then used to split the laser into substantially orthogonally polarized first and second component laser beams. The polarizing optical component is aligned such that the second component laser beam has the predetermined polarization, such that all of the energy of the laser beam is provided in the second component laser beam when no particle passes through the laser beam. In the particle sensor of the present invention, first and second photodetectors are positioned for detecting, respectively, the intensities of the first and second component laser beams to detect a phase shift of the laser beam caused by a particle passing through the laser beam.

According to another aspect of the present invention, a first beam splitter is provided for splitting the laser beam into orthogonally polarized two component laser beams separated by a predetermined distance prior to being focussed to pass through the space in which particles are to be detected. The component laser beams are then focussed so as to be substantially parallel over the distance the component laser beams pass in the space of particle detection. Splitting the laser beam into the two component laser beams allow the detection of both spherical and non-spherical particles.

According to another aspect of the present invention, a first detector is provided to receive the incident laser beam to serve as a reference for canceling laser noise.

The particle sensors of the present invention can be improved by (i) using a narrow band optical filter to remove noise from background light; (ii) using a collimating tube for limiting the size of the viewed aperture in said space; and (iii) attenuating the light detected by photodetector receiving the main beam, so as to allow the photodetector to operate in a substantially linear regime.

The present invention is better understood after considering the detailed description below, in conjunction with the accompanying drawings.

DETAILED DESCRIPTION OF THE PREFERRED EMBODIMENTS

Figure 1:
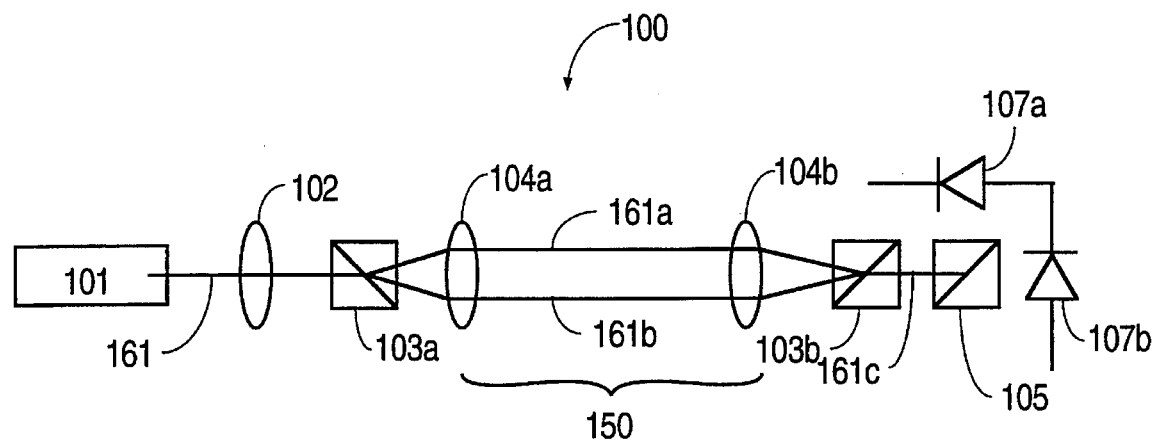
FIG. 1 shows a particle detector 100 in which a laser beam 161 is projected through a space 150 in which particles to be detected are present; laser beam 161 is detected by two photo cells 107a and 107b placed to receive orthogonal polarizations of light, in accordance with the present invention.

FIG. 1 shows an embodiment of the present invention in which particle detector 100 projects a laser beam 161 through space 150 in which the particles to be detected are. As shown in FIG. 1, laser source 101 projects a polarized laser beam 161 through collimating lens 102 to form a laser beam of parallel rays. Typically, laser source 101 is a low noise laser diode, such as the Sony 301, available from Sony Corporation, Japan. Sony 301 operates at a power of 50 mW, and provides a laser beam of wavelength of about 800 nanometers. Laser diodes, such as the Sony 301, have typical polarization ratios in excess of 1000. A number of commercially available lenses are suitable to be used as collimating lens 102; for example, collimating lens 102 can be made from SPL lens available from Nippon Sheet Glass of Tokyo, Japan.

Laser beam 161 is polarized at 45° to the paper, so that the components of laser beam 161, i.e. the components of laser beam 161 in the plane of the paper and perpendicular to the plane of the paper, are of equal power. Polarized laser beam 161 then passes through Wollaston prism 103a, which splits laser beam 161 into laser beams 161a and 161b, which are orthogonally polarized with respect to each other. A suitable wallaston prism for Wollaston prism 103a is model WQ12-05 from Karl Lambrecht, Inc. of Chicago, Ill. This Wollaston prism provides a splitting of 0.5°, resulting in laser beams 161a and 161b being separated by about 1 mm at the 75 mm focal length of lens 104a.

Laser beams 161a and 161b emerge at an angle with respect to each other from Wollaston prism 103a. This angle between laser beams 161a and 161b is typically a few tenths of a degree. Laser beams 161a and 161b then pass through lens 104a, which converts laser beams 161a and 161b to essentially parallel beams without affecting their relative polarization.

After passing through space 150, laser beams 161a and 161b are then combined by lens 104b and Wollaston prism 103b. Lens 104b and Wollaston prism 103b are each substantially identical to lens 104a and Wollaston prism 103a to form a combined laser beam 161c of 45° polarization. Lens 104a and 104b are common cylindrical lenses with focal lengths chosen to provide the necessary length of substantially parallel beam through the area of particle detection. The combined laser beam 161c then passes through a polarizing beam splitting cube 105 oriented so that, when no particles are detected, the combined laser beam 161c impinges only on photocell 107b. A suitable polarizing beam splitting cube for use as polarizing beam splitting cube 105 is model TFPC 12 from Karl Lambrecht, Inc., which provides a selectivity between polarizations of better than 1000.

Figure 2A:
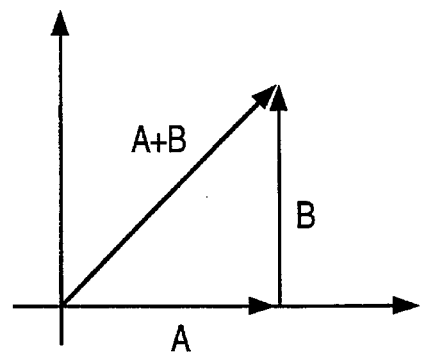
FIG. 2a shows that, when no particle is present in either laser beam 161a or 161b, the combined laser beam 161c has a polarization of 45°.

The operation of particle monitor 100 is next disclosed. When neither laser beam 161a nor laser beam 161b encounters a particle, laser beams 161a and 161b each have substantially equal intensity, so that the combined laser beam 161c has a polarization angle of 45° as shown in FIG. 2a. FIG. 2a shows the polarization of laser beam 161c, as a vector sum of orthogonally polarized laser beams 161a and 161b, when no particle is present in either laser beam 161a or laser beam 161b.

Figure 2B:
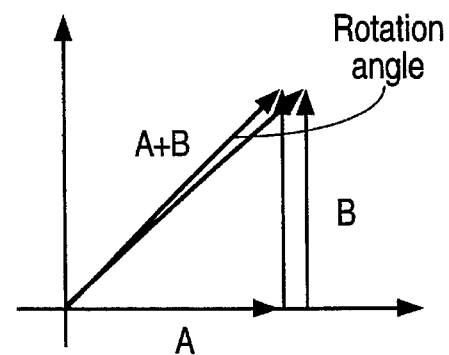
FIG. 2b shows the change in polarization in combined laser beam 161c as a result of a particle passing through one of laser beams 161a and 161b.

However, when a particle is encountered by laser beam 161a, the intensity of laser beam 161a is reduced. As a result, the combined laser beam 161c will have a polarization other than 45°, as shown in FIG. 2b FIG. 2b shows the polarization of laser beam 161c, as a vector sum of laser beams 161a and 161b, when the intensity of laser beam 161a is reduced due to the presence of a particle in laser beam 161a. Consequently, the combined laser beam 161c entering polarizing beam splitting cube 105 is split, and the component split from combined laser beam 161c impinges onto photocell 107a to cause a photo current in photo cell 107a, thereby indicating the presence of a particle.

Since laser beam 161c impinges on photocell 107b, particle monitor 100 is substantially a bright field detector. Hence, the present invention allows detection of particles in "bright field" particle monitor 100. However, in particle monitor 100, photocell 107a receives incident light beam from the combined laser beam 161c, only when a particle passes through either laser beam 161a or 161b. Thus, no shot noise is generated in photocell 107a. Consequently, sensitivity of particle monitor 100, unlike other bright field sensors, does not suffer degraded performance due to shot noise.

Furthermore, photocell 107b which receives the total energy of combined laser beam 161c, when there is not a particle in either laser beam 161a or 161b, can be used as a noise reference to cancel laser noise. Thus, particle monitor 100, whose primary noise component is amplifier noise, achieves both the sensitivity of a dark field sensor, and the advantages of a bright field particle sensor.

Particle monitor 100 detects both radially symmetrical and asymmetrical particles. In some applications, detecting only asymmetrical particles, rather than both, is sufficient. In such applications, laser beam 161 need not be split into laser beams 161a and 161b. Indeed, in the applications of interest, i.e. particle detection in semiconductor manufacturing equipment, particles are seldom spherical. To understand why a single laser beam does not detect radially symmetrical particles, consider the case where laser beams 161A and 161B are brought closer and closer together, until they overlap. Now, if a spherical particle pass through the overlapped beams, the particle scatters equally both laser beam 161a and 161b, i.e. both polarization components. The resulting polarization in laser beams 161c does not rotate under this condition, and no signal is generated at photocell 107a. However, a non-spherical particle scatters preferentially one polarization more than the orthogonal polarization. For instance, a rod-shaped particle scatters light polarized along the axis of the rod less preferentially than light polarized off-axis. Thus, the resulting polarization of laser beam 161c scattered by a rod-shaped particle is rotated, and a single beam is sufficient to detect the presence of such a particle. A single-beam particle monitor can be achieved for detection of non-spherical particles by omitting the Wollaston prisms 103a and 103b.

In applications where corrosive gasses are present, sapphire windows are placed on the chamber side of lenses 104a and 104b. Sapphire of 0001 crystal orientation is chosen for these windows, since this crystal orientation of sapphire does not affect the polarization of the laser beam passing through it, and sapphire is not significantly attacked by corrosive species, such as fluorine and reactive fluorine by-products common found in a plasma etcher.

Performance of particle monitor 100 can be calculated by determining the amount of light a particle scatters from laser beam 161, when a single beam is used, or from one of its component beams 161a and 161b, when two laser beams are used. The light reaching the detection photocell 107a is a function of the amount of light scattered by the particle passing through laser beam 161 or the component laser beams 161a and 161b. The noise in the detection photocell 107a is determined by shot noise, resulting from background light reaching the detection photocell 107a. Such background light can be caused by imperfection in the laser polarization components, i.e. laser source 101 and Wollaston prisms 103a and 103b, and polarizing beam splitter cubes 106. With the signal and noise intensities known, the signal to noise ratio is determined.

For a typical system, laser beam 161 is focussed to a thickness $$t_0 = \frac{\lambda f}{\pi t_1} \qquad (2)$$

where $t_1$ is the thickness at the lens, $\lambda$ is the wavelength, and f the focal length.

In a typical system with a focal length of 7.5 cm and a beam thickness of 1 mm at the lens, the beam thickness at laser beam 161's focus is approximately 0.004 cm. The typical beam width is 3 mm, which remains constant through the system.

The scattering cross-section for a particle is easily calculated using Mie scattering theory. A discussion of the Mie scattering theory is found in "Light Scattering by Small Particles" by H. C. van de Hulst, published by Dover books. The noise level is calculated using equation (1) given above, with the bandwidth given by the equation $$BW = \frac{0.3v}{t_0}, \qquad (3)$$

where v is the particle velocity.

Equation (3) depends on the relation that the pulse width generated by a particle passing through the beam depends upon the particle velocity and the thickness to the beam. The factor of 0.3 arises because the pulse is Gaussian rather than sinusoidal in shape and represents a ½ cycle.

Figure 3:
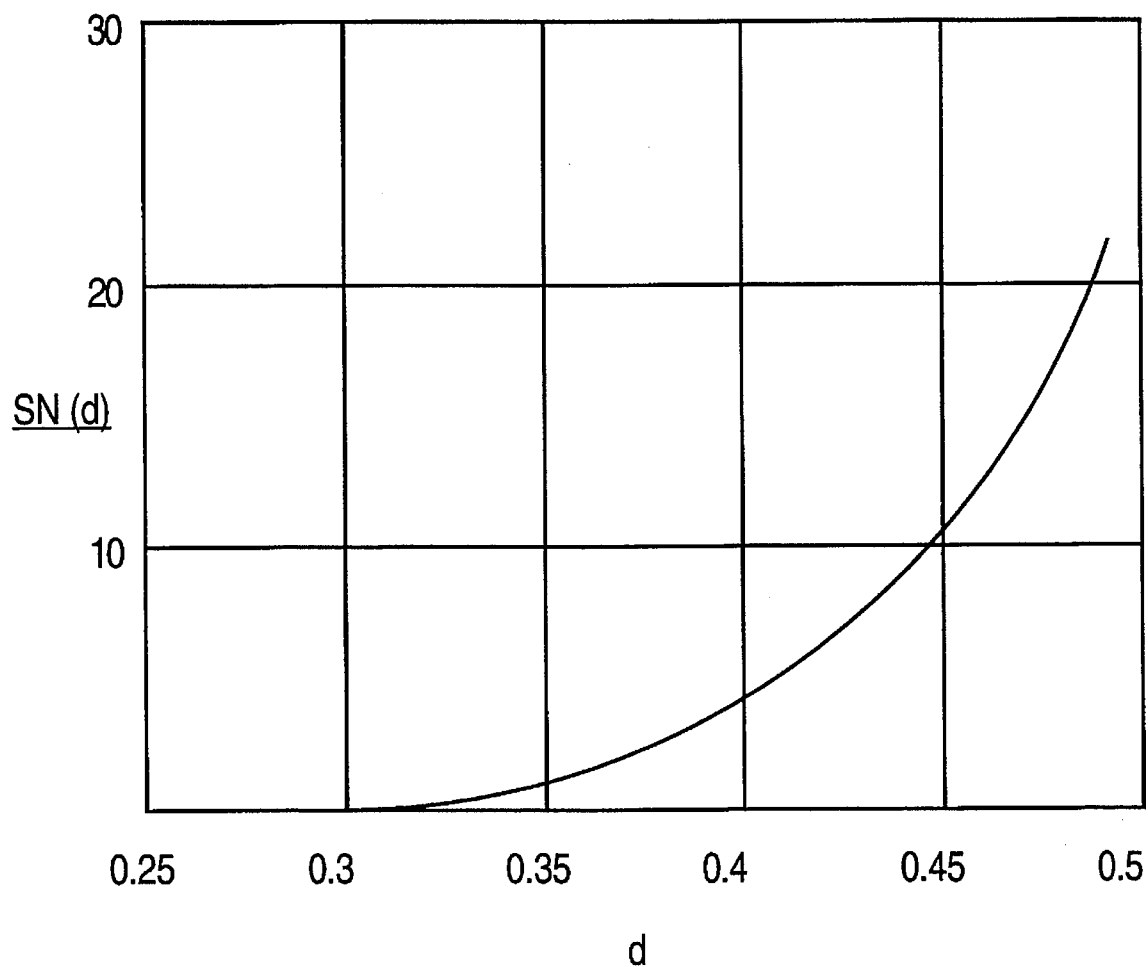
FIG. 3 is a graph plotting the signal-to-noise (s/n) ratio versus the particle size detectable by particle monitor 100.

Using these factors, and assuming that (a) the main beam is attenuated by a factor of 1000 in reference photocell 107b and (b) photocell 107a's responsivity is 0.5 amps/watt, the graph in FIG. 3 plot the signal-to-noise (s/n) ratio versus particle size in microns for particles with an index of refraction of 1.5. A s/n ratio greater than 2 is normally needed to detect a particle.

Figure 4:
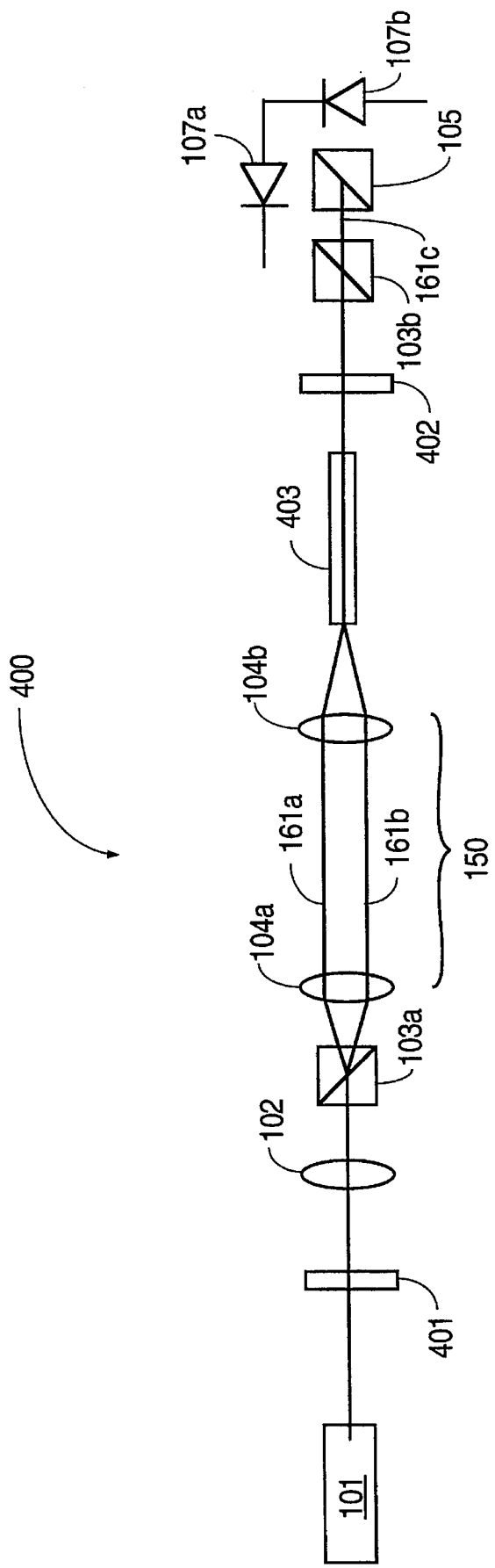
FIG. 4 shows a particle monitor 400 which is a variation in configuration of particle monitor 100 shown in FIG. 1.
Figure 5:
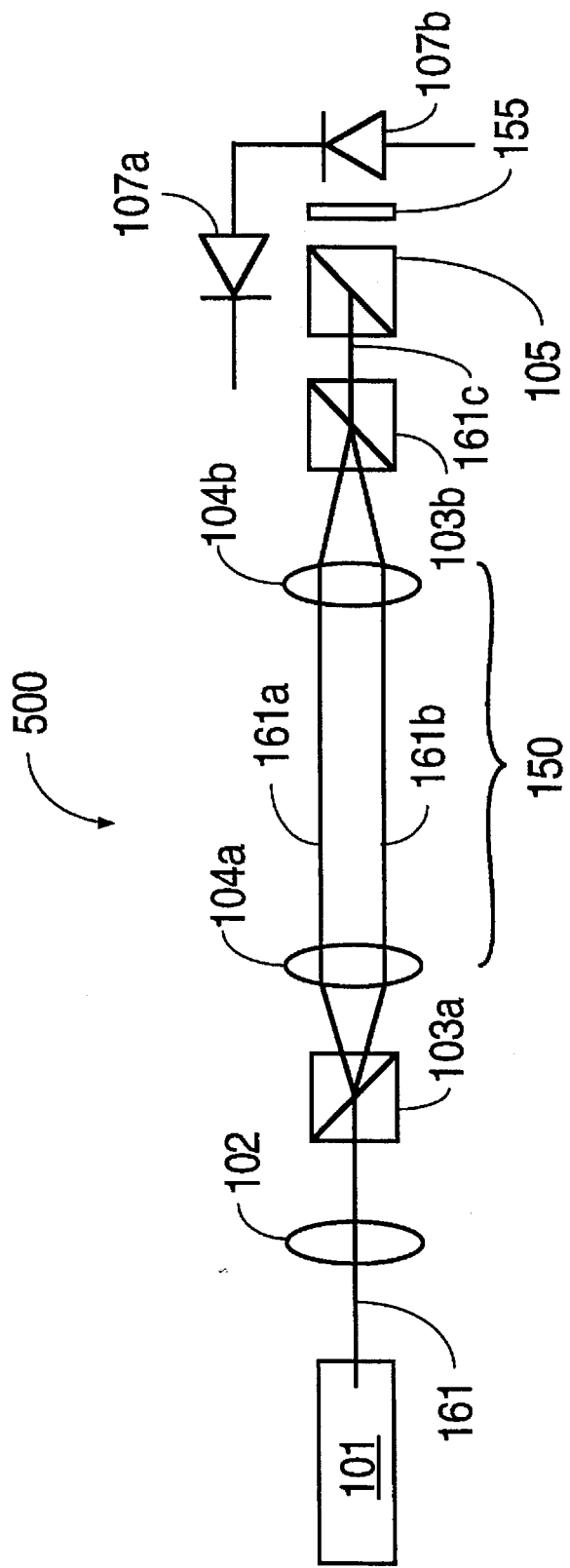
FIG. 5 shows a particle monitor which will attenuate the light detected by said first photodetector, such that said photodetector operates in a substantially linear regime.

In practice, performance of particle monitor 100 can be enhanced by the following variation in its configuration such as illustrated by particle monitor 400 in FIG. 4, or particle monitor 500 in FIG. 5.

(i) a polarizer can be placed after laser source 101 to remove polarization 40 noise. A good polarizer to be used is a beam splitting cube oriented so that any radiation from laser source 101 out of the primary polarization is directed 90° out of the system;

(ii) a narrow band optical filter 402 can be placed before the final detector photocell 107a to remove optical noise from the ambient;

(iii) laser beam 161 can run through a long, narrow tube 403 prior to reaching the receiver optics (e.g. Wollaston prism 103b) to limit the viewed aperture, thereby restricting the amount of background noise that enters particle monitor 100;

(v) the signal from reference photocell 107b can be used in a circuit to cancel the laser noise; and (vi) adding means 155 to attenuate the signal of reference photocell 107b to maintain linearity when using high laser powers.

The above detailed description is provided to illustrate the specific embodiments of the present invention and should not be construed as limiting. Numerous variations and modifications are possible within the scope of the present invention the present invention is defined by the following claims:

We claim:

1. A particle sensor, comprising:

a laser source for providing a laser beam of a predetermined linear polarization;

an optical component, receiving said laser beam, for focusing said laser beam to pass through an area of space in which particles to be detected are present;

means, positioned to receive said laser beam from said optical component, for splitting said laser beam into substantially orthogonally polarized first and second component laser beams, said means for splitting said laser beam oriented to provide said second component laser beam with said predetermined linear polarization, such that said first component laser beam has insignificant intensity at said predetermined linear polarization; and first and second photodetectors positioned for detecting, respectively, intensities of said first and second component laser beams.

2. A particle sensor as in claim 1, wherein said source of laser is a laser diode.

3. A particle sensor as in claim 1, wherein said means for splitting said laser beam comprises a polarizing beam splitter.

4. A particle sensor as in claim 1, wherein said optical component comprises:

a first beam splitter for splitting said laser beam into orthogonally polarized third and fourth component laser beams separated by a predetermined distance;

a focussing optical component, positioned to receive said third and fourth component laser beams, for focussing said third and fourth laser beams, such that said third and fourth laser beams are substantially parallel through said space; and means, positioned to received said substantially parallel third and fourth laser beams, for combining said third and fourth laser beams into a single laser beam.

5. A particle sensor as in claim 1, wherein said optical component includes a polarizer for removing polarization noise in the laser beam.

6. A particle sensor as in claim 1, wherein an intensity detected in said first photodetector serves as a reference intensity used to cancel laser noise.

7. A particle sensor as in claim 1, further comprising a narrow band optical filter positioned in said laser beam's path before said first and second photodetectors for removing noise from background light.

8. A particle sensor as in claim 1, further comprising a collimating tube positioned between said optical component and said means for splitting said laser beam for limiting a viewed aperture in said space.

9. A particle sensor as in claim 6, said particle sensor further comprising means for attenuating the light detected by said first photodetector, such that said photodetector operates in a substantially linear regime.

10. A method for providing a particle sensor, comprising the steps of:

providing a laser beam of a predetermined linear polarization;

focusing said laser beam to pass through an area of space in which particles to be detected are present;

splitting said laser beam into substantially orthogonally polarized first and second component laser beams, said step of splitting said laser beam providing said second component laser beam with said predetermined linear polarization, such that said first component laser beam has insignificant intensity at said predetermined linear polarization; and positioning first and second photodetectors for detecting, respectively, intensities of said first and second component laser beams.

11. A method as in claim 10, wherein said step of providing a laser beam utilizes a laser diode.

12. A method as in claim 10, wherein said step of splitting said laser beam comprises the step of utilizing a polarizing beam splitter.

13. A method as in claim 10, wherein said step of focussing comprises the steps of:

splitting said laser beam into orthogonally polarized third and fourth component laser beams separated by a predetermined distance;

focussing said third and fourth laser beams, such that said third and fourth laser beams are substantially parallel through said space; and combining said third and fourth laser beams into a single laser beam.

14. A method as in claim 10, wherein said focussing step provides a polarizer for removing polarization noise in the laser beam.

15. A method as in claim 10, wherein said step of providing first and second photodetector utilizes an intensity detected in said first photodetector as a reference intensity for canceling laser noise.

16. A method as in claim 10, further comprising the step of providing a narrow band optical filter positioned in said laser beam's path before said first and second photodetectors for removing noise from background light.

17. A method as in claim 10, further comprising the step of utilizing a collimator tube prior to said step of splitting said laser beam for limiting a viewed aperture in said space.

18. A method as in claim 15, wherein said step of providing first and second photodetectors attenuates the light detected by said first photodetector, such that said photodetector operates in a substantially linear regime.

* * * * *